US012496440B2

(12) United States Patent
Wise et al.

(10) Patent No.: US 12,496,440 B2
(45) Date of Patent: Dec. 16, 2025

(54) APPARATUS AND METHODS FOR MAKING COCHLEAR IMPLANT ELECTRODE ARRAYS

(71) Applicant: ADVANCED BIONICS AG, Staefa (CH)

(72) Inventors: Nicholas Wise, Pasadena, CA (US); Uli Gommel, Valencia, CA (US); Martin Sandoval-Perez, Canyon Country, CA (US); Morgan Gegg, Ventura, CA (US)

(73) Assignee: Advanced Bionics AG, Staefa (CH)

( * ) Notice: Subject to any disclaimer, the term of this patent is extended or adjusted under 35 U.S.C. 154(b) by 1060 days.

(21) Appl. No.: 17/232,131

(22) Filed: Apr. 15, 2021

(65) Prior Publication Data

US 2021/0236808 A1 Aug. 5, 2021

Related U.S. Application Data

(63) Continuation-in-part of application No. 16/599,102, filed on Oct. 10, 2019, now Pat. No. 11,452,865.

(51) Int. Cl.

| | |
|---|---|
| ***A61N 1/05*** | (2006.01) |
| ***A61N 1/36*** | (2006.01) |
| ***H01R 4/02*** | (2006.01) |
| ***H01R 4/10*** | (2006.01) |

(Continued)

(52) U.S. Cl.

CPC ....... *A61N 1/0541* (2013.01); *A61N 1/36038* (2017.08); *H01R 4/029* (2013.01); *H01R 4/10* (2013.01); *H01R 43/02* (2013.01); *H01R 43/007* (2013.01); *H01R 2201/12* (2013.01)

(58) Field of Classification Search

CPC .. A61N 1/0541; A61N 1/36038; H01R 4/029; H01R 4/10; H01R 43/02; H01R 43/007; H01R 2201/12

See application file for complete search history.

(56) References Cited

U.S. PATENT DOCUMENTS

| | | | |
|---|---|---|---|
| 4,686,765 | A | 8/1987 | Byers et al. |
| 4,819,647 | A | 4/1989 | Byers et al. |

(Continued)

FOREIGN PATENT DOCUMENTS

| | | | |
|---|---|---|---|
| WO | WO2012154256 | A1 | 11/2012 |
| WO | WO2015030734 | A1 | 3/2015 |

(Continued)

*Primary Examiner* — Jeffrey T Carley

(74) *Attorney, Agent, or Firm* — Henricks Slavin LLP

(57) ABSTRACT

A method including the steps of securing a plurality of contact subassemblies to a mold surface at longitudinally spaced locations within a mold with resilient material located between the contact subassemblies and the mold surface, the contact subassemblies including, prior to being placed into the mold, an electrically conductive contact having a flat portion defining lateral ends and side portions associated with the lateral ends of the flat portion and a lead wire secured to the electrically conductive contact, introducing resilient material into the mold to form an electrode array blank including a flexible body defining an exterior surface and the electrically conductive contacts below the exterior, and forming a plurality of windows in the electrode array blank that extend through the exterior surface of the flexible body to the electrically conductive contacts.

14 Claims, 11 Drawing Sheets

(51) Int. Cl.
*H01R 43/02* (2006.01)
*H01R 43/00* (2006.01)

(56) References Cited

U.S. PATENT DOCUMENTS

| | | | | |
|---|---|---|---|---|
| 4,961,434 | A * | 10/1990 | Stypulkowski | A61N 1/0541 607/137 |
| 5,000,194 | A | 3/1991 | Van Den Honert et al. | |
| 5,037,497 | A | 8/1991 | Stypulkowski | |
| 5,123,422 | A | 6/1992 | Charvin | |
| 5,439,485 | A | 8/1995 | Mar et al. | |
| 5,534,022 | A | 7/1996 | Hoffmann et al. | |
| 5,542,173 | A | 8/1996 | Mar et al. | |
| 5,580,699 | A * | 12/1996 | Layman | A61N 1/05 430/311 |
| 5,658,709 | A | 8/1997 | Layman et al. | |
| 5,824,022 | A | 10/1998 | Zilberman et al. | |
| 5,999,859 | A | 12/1999 | Jolly | |
| 6,119,044 | A * | 9/2000 | Kuzma | A61N 1/0541 607/137 |
| 6,125,302 | A | 9/2000 | Kuzma | |
| 6,129,753 | A | 10/2000 | Kuzma | |
| 6,144,883 | A | 11/2000 | Kuzma | |
| 6,195,586 | B1 | 2/2001 | Kuzma | |
| 6,304,787 | B1 | 10/2001 | Kuzma et al. | |
| 6,309,410 | B1 * | 10/2001 | Kuzma | A61N 1/0541 607/137 |
| 6,374,143 | B1 | 4/2002 | Berrang et al. | |
| 6,421,569 | B1 | 7/2002 | Treaba et al. | |
| 6,862,805 | B1 | 3/2005 | Kuzma et al. | |
| 6,889,094 | B1 | 5/2005 | Kuzma et al. | |
| 7,451,000 | B2 | 11/2008 | Gibson et al. | |
| 8,461,042 | B2 * | 6/2013 | Dadd | B23K 26/36 438/690 |
| 8,620,459 | B2 | 12/2013 | Gibson et al. | |
| 8,782,884 | B2 | 7/2014 | Capcelea et al. | |
| 8,880,193 | B1 * | 11/2014 | Thenuwara | A61N 1/0541 607/57 |
| 9,694,174 | B2 | 7/2017 | Dadd et al. | |
| 10,406,350 | B2 | 9/2019 | Mercanzini et al. | |
| 11,103,703 | B2 | 8/2021 | Krywcun et al. | |
| 11,198,014 | B2 * | 12/2021 | Stevenson | B23K 35/3013 |
| 11,452,865 | B2 | 9/2022 | Clabeaux et al. | |
| 11,471,668 | B2 | 10/2022 | Salvatierra et al. | |
| 11,986,654 | B2 | 5/2024 | Krywcun et al. | |
| 2003/0171787 | A1 | 9/2003 | Money et al. | |
| 2004/0015221 | A1 * | 1/2004 | Kuzma | B29C 33/126 607/116 |
| 2005/0234535 | A1 * | 10/2005 | Risi | A61N 1/0541 607/57 |
| 2006/0035499 | A1 * | 2/2006 | Johnson | H02G 3/00 439/215 |
| 2009/0306745 | A1 | 12/2009 | Parker et al. | |
| 2010/0036470 | A1 * | 2/2010 | Nielsen | B22F 10/28 607/137 |
| 2010/0287770 | A1 * | 11/2010 | Dadd | A61N 1/0541 29/877 |
| 2011/0016710 | A1 * | 1/2011 | Dadd | A61N 1/0541 29/874 |
| 2011/0126410 | A1 * | 6/2011 | Capcelea | B29C 45/0055 29/746 |
| 2011/0130815 | A1 * | 6/2011 | Gibson | B23K 26/40 29/874 |
| 2011/0313269 | A1 | 12/2011 | Kim et al. | |
| 2012/0315798 | A1 * | 12/2012 | Poon | H01R 24/58 439/668 |
| 2013/0079749 | A1 | 3/2013 | Overstreet et al. | |
| 2013/0238074 | A1 * | 9/2013 | Zimmerling | A61N 1/0541 607/137 |
| 2014/0094892 | A1 | 4/2014 | Thenuwara et al. | |
| 2014/0163662 | A1 | 6/2014 | Beerling et al. | |
| 2015/0032194 | A1 | 1/2015 | Mergen et al. | |
| 2015/0148736 | A1 | 5/2015 | Jolly et al. | |
| 2015/0246234 | A1 | 9/2015 | Hazard et al. | |
| 2016/0022990 | A1 | 1/2016 | Risi | |
| 2016/0082249 | A1 | 3/2016 | Thenuwara et al. | |
| 2016/0193460 | A1 | 7/2016 | Xu et al. | |
| 2017/0056646 | A1 | 3/2017 | Sibary et al. | |
| 2020/0188666 | A1 | 6/2020 | Krywcun et al. | |
| 2020/0238092 | A1 * | 7/2020 | Henschel | A61N 1/3754 |
| 2020/0384262 | A1 | 12/2020 | Hoffman et al. | |
| 2021/0106816 | A1 | 4/2021 | Clabeaux et al. | |
| 2021/0187282 | A1 | 6/2021 | Salvatierra | |
| 2021/0346697 | A1 | 11/2021 | Krywcun et al. | |

FOREIGN PATENT DOCUMENTS

| | | | | |
|---|---|---|---|---|
| WO | WO-2018031025 | A1 * | 2/2018 | A61N 1/0541 |
| WO | WO2018/102695 | A2 | 6/2018 | |
| WO | WO 2018/209872 | A1 | 11/2018 | |

* cited by examiner

APPARATUS AND METHODS FOR MAKING COCHLEAR IMPLANT ELECTRODE ARRAYS

CROSS-REFERENCE TO RELATED APPLICATIONS

This application is a continuation-in-part of U.S. application Ser. No. 16/599,102, filed Oct. 10, 2019, which is incorporated herein by reference in its entirety.

BACKGROUND

1. Field

The present disclosure relates generally to the implantable portion of implantable cochlear stimulation (or "ICS") systems and, in particular, to electrode arrays.

2. Description of the Related Art

Referring to FIGS. 1 and 2, the cochlea 10 is a hollow, helically coiled, tubular bone (similar to a nautilus shell) that is divided into the scala vestibuli 12, the scala tympani 14 and the scala media 16 by the Reissner's membrane 18 and the basilar membrane 20. The cochlea 10, which typically includes approximately two and a half helical turns, is filled with a fluid that moves in response to the vibrations coming from the middle ear. As the fluid moves, a tectorial membrane 22 and thousands of hair cells 24 are set in motion. The hair cells 24 convert that motion to electrical signals that are communicated via neurotransmitters to the auditory nerve 26, and transformed into electrical impulses known as action potentials, which are propagated to structures in the brainstem for further processing. Many profoundly deaf people have sensorineural hearing loss that can arise from the absence or the destruction of the hair cells 24 in the cochlea 10. Other aspects of the cochlea 10 illustrated in FIGS. 1 and 2 include the medial wall 28, the lateral wall 30 and the modiolus 32.

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable lead with an electrode array that is inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant") having a lead with an electrode array, a sound processor unit (e.g., a body worn processor or behind-the-ear processor) that communicates with the cochlear implant, and a microphone that is part of, or is in communication with, the sound processor unit. The cochlear implant electrode array, which is formed by a molding process, includes a flexible body formed from a resilient material and a plurality of electrically conductive contacts (e.g., sixteen platinum contacts) spaced along a surface of the flexible body. The contacts of the array are connected to lead wires that extend through the flexible body. Exemplary cochlear leads and exemplary lead manufacturing methods are illustrated in WO2018/031025A1 and WO2018/102695A1, which are incorporated herein by reference.

The present inventors have determined that conventional cochlear implant electrode arrays, as well as conventional methods of manufacturing such arrays, are susceptible to improvement. For example, the present inventors have determined that it would be desirable to form contacts and connect lead wires to the contacts prior to placing the contacts into the mold, to employ contacts that can be formed in relatively simple dies, and to more precisely orient the contacts within the mold.

Another issue is related to the fact that it is typically intended that after the electrode array is implanted within the cochlea, the contacts will all face the modiolus in the cochlea, which is where the spiral ganglion cells that innervate the hair cells are located. The cochlear anatomy can, however, cause the electrode array to twist as it is inserted deeper into the cochlea. The degree and location of twisting can vary from patient to patient and depends on each patient's anatomy and the length of the electrode array. The perception of sound may be adversely impacted in those instances where twisting of the electrode array results in some or all of the contacts not facing the modiolus. The efficiency of the cochlear implant system is also adversely effected, e.g., battery life is reduced, when the contacts are not facing the modiolus because higher current may be required (as compared to a properly oriented electrode array) for the patient to perceive a particular level of loudness.

SUMMARY

A method in accordance with one of the present inventions includes the steps of securing a plurality of contact subassemblies to a mold surface at longitudinally spaced locations within a mold with resilient material located between the contact subassemblies and the mold surface, the contact subassemblies including, prior to being placed into the mold, an electrically conductive contact having a flat portion defining lateral ends and side portions associated with the lateral ends of the flat portion and a lead wire secured to the electrically conductive contact, introducing resilient material into the mold to form an electrode array blank including a flexible body defining an exterior surface and the electrically conductive contacts below the exterior, and forming a plurality of windows in the electrode array blank that extend through the exterior surface of the flexible body to the electrically conductive contacts.

A method in accordance with one of the present inventions includes the steps of positioning an electrically conductive workpiece onto a die having a base, with a flat surface, and side members extending from the base, inserting a lead wire into the electrically conductive workpiece, and after the positioning step, compressing the electrically conductive workpiece onto the lead wire to form electrode array contact subassembly that includes an electrically conductive contact having a flat portion defining lateral ends and side portions associated with the lateral ends of the flat portion and a lead wire secured to the electrically conductive contact.

There are a number of advantages associated with such methods. By way of example, but not limitation, forming the contact subassembly in a die (as opposed to compressing a workpiece within the electrode array mold) prevents damage to the mold, allows contacts that are smaller than the associated portion of the mold and/or differently shaped than the associated portion of the mold to be employed, and allows damaged or otherwise non-conforming contacts to be identified and discarded prior to their inclusion in an electrode array. There are also advantages associated with the contacts having a flat portion. For example, the flat portion facilitates the use of a relatively simple die, increases the likelihood that the lead wire will be captured at its intended location within contact, reduces the likelihood that the contact will be pivot out of its intended orientation within the mold, and facilitates more accurate orientation of laser ablation systems in those instances where laser ablation systems are used to remove material from an electrode array blank to expose portions of the contacts.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 2:
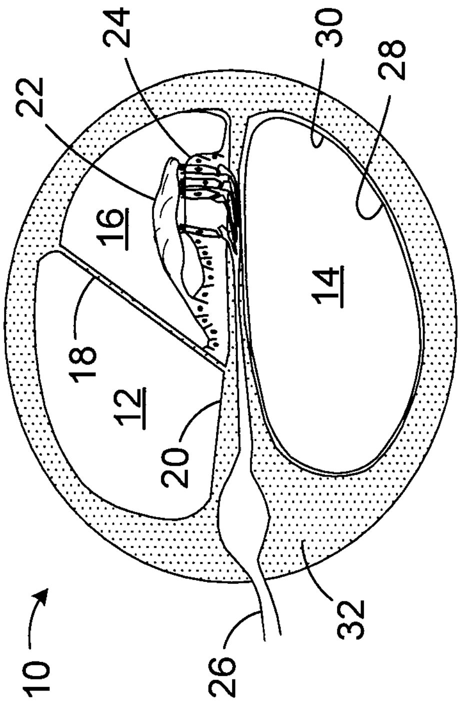
FIG. 2 is another section view of the cochlea.
Figure 1:
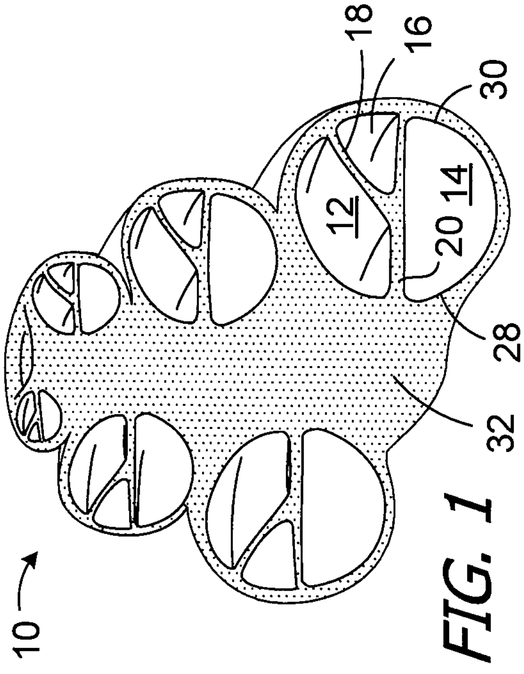
FIG. 1 is a section view of a cochlea.
Figure 3:
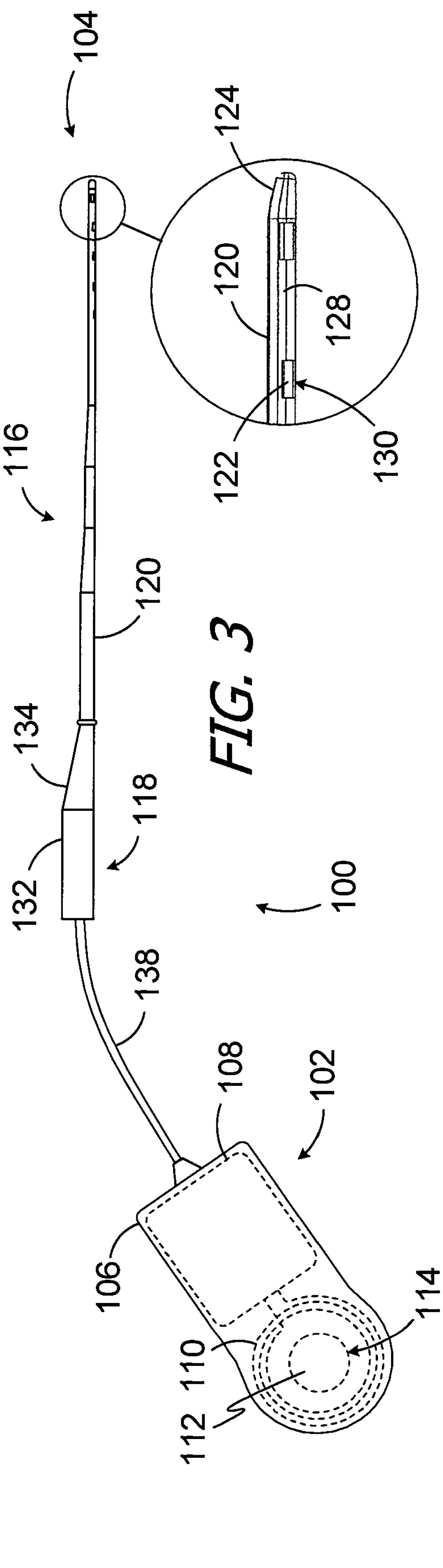
FIG. 3 is a plan view of a cochlear implant in accordance with one embodiment of a present invention.
Figure 4:
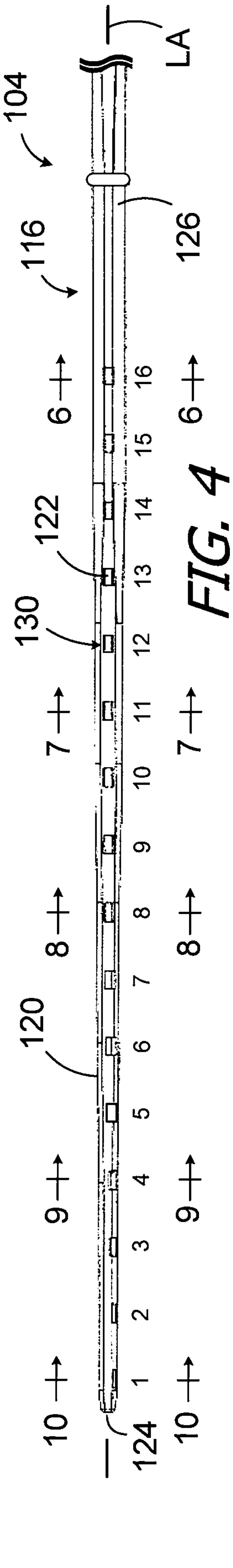
FIG. 4 is a bottom view of a cochlear lead electrode array in accordance with one embodiment of a present invention.
Figure 5:
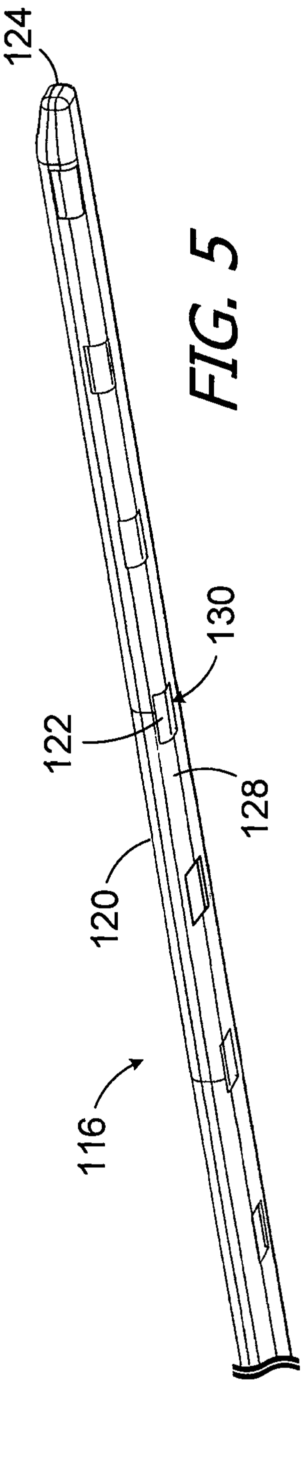
FIG. 5 is a perspective view of a portion of the cochlear lead electrode array illustrated in FIG. 4.

One example of a cochlear implant (or "implantable cochlear stimulator") in accordance with at least some of the present inventions is illustrated in FIGS. 3-10. Referring first to FIGS. 3-5, the exemplary cochlear implant 100 includes a stimulation assembly 102 and a cochlear lead 104.

A wide variety of stimulation assemblies may be combined with the present cochlear leads. The exemplary stimulation assembly 102 illustrated in FIG. 3 includes a flexible housing 106 formed from a silicone elastomer or other suitable material, a processor assembly 108, an antenna 110 that may be used to receive data and power by way of an external antenna that is associated with, for example, a sound processor unit, and a positioning magnet 112 located within a magnet pocket 114. The magnet 112 is used to maintain the position of a sound processor headpiece over the antenna 110. The cochlear implant may, in some instances, be configured is manner that facilitates magnet removal and replacement. Here, the housing 106 may be provided with a magnet aperture (not shown) that extends from the magnet pocket 114 to the exterior of the housing.

The exemplary cochlear lead 104 illustrated in FIGS. 3-5 includes an electrode array 116 and, in at least some instances, a wing 118 that functions as a handle for the surgeon during the implantation surgery. The exemplary electrode array 116 has a flexible body 120 and a plurality of electrically conductive contacts 122 (e.g., the sixteen contacts 122 illustrated in FIG. 4) spaced along the flexible body between the tip (or "apical") end 124 and the base (or "basal") end 126. The electrically conductive contacts 122 (or "contacts") may be located inward of the flexibly body outer surface 128 and exposed by way of a corresponding plurality of contact windows (or "windows") 130 that extend through the outer surface of the flexible body to the contacts. The windows 130 may be perimetrically aligned with one another in some implementations. Alternatively, and as is discussed in greater detail with references to FIGS. 6-10, one or more of the windows 130 may be perimetrically offset from other windows when the electrode array 116 is in a state where the electrode array 116 is straight and is not twisted around its longitudinal axis LA (see FIGS. 3 and 4) by torsional forces. The perimetric offsets may be used to account for twisting of the electrode array 116 that occurs during insertion. If, for example, a contact 122 is on a portion of the flexible body 120 that is expected to twist 50° around the longitudinal axis during the insertion, then the associated window 130 may be perimetrically offset by 50° in the opposite direction from what would have been its untwisted location. This allows the present cochlear leads 104 to be configured, e.g., based in part on patient-specific information or averages associated with known insertion data, in such manner that the portions of the electrode array contacts 122 exposed by the windows 130 will face the modiolus within the cochlea after implantation despite twisting of the electrode array around the longitudinal axis LA. As a result, the present cochlear leads will not adversely impact the patient's perception of sound or the efficiency of the associated cochlear implant system, as can be the case with cochlear leads having contacts that do not face the modiolus when the electrode array twists during insertion.

The wing 118 of the exemplary cochlear lead 104 illustrated in FIGS. 3-5 may include a rectangular portion 132 and a tapered portion 134 and, in addition to functioning as a handle, the wing provides tension relief for lead wires 136 (FIGS. 5A and 6) that do not run straight through the wing. A tubular member 138, which may consist of tubes of different sizes, extends from the wing 118 to the stimulation assembly housing 106. The contacts 122 are connected to the lead wires 136 in the manner described below, and the lead wires extend through the flexible body 120 and tubular member 138 to a connector (not shown) in the housing 106. The connection between the stimulation assembly 102 and a cochlear lead 104 may be a temporary connection, whereby the stimulation assembly and a cochlear lead may be disconnected from one another (e.g., for in situ replacement of the stimulation assembly), or a permanent connection.

Although the present inventions are not so limited, the flexible body 120 of the exemplary electrode array 116 has a non-circular shape with a flat bottom (note FIGS. 6-10) in a cross-section perpendicular to the longitudinal axis LA. The flexible body 120 may also be tapered, with a perimeter in a plane perpendicular to the longitudinal axis LA that is smaller at the tip end 124 than at the base end 126. The shape of the flexible body 120 also varies along the length of the flexible body. Any other suitable flexible body shapes (e.g., circular or oval), with or without a flat surface, may also be employed. Suitable materials for the flexible body 120 include, but are not limited to, electrically non-conductive resilient materials such as LSR, high temperature vulcanization ("HTV") silicone rubbers, room temperature vulcanization ("RTV") silicone rubbers, and thermoplastic elastomers ("TPEs").

Figures 5A, 5B, 5C, 5D, 5E, 5F:
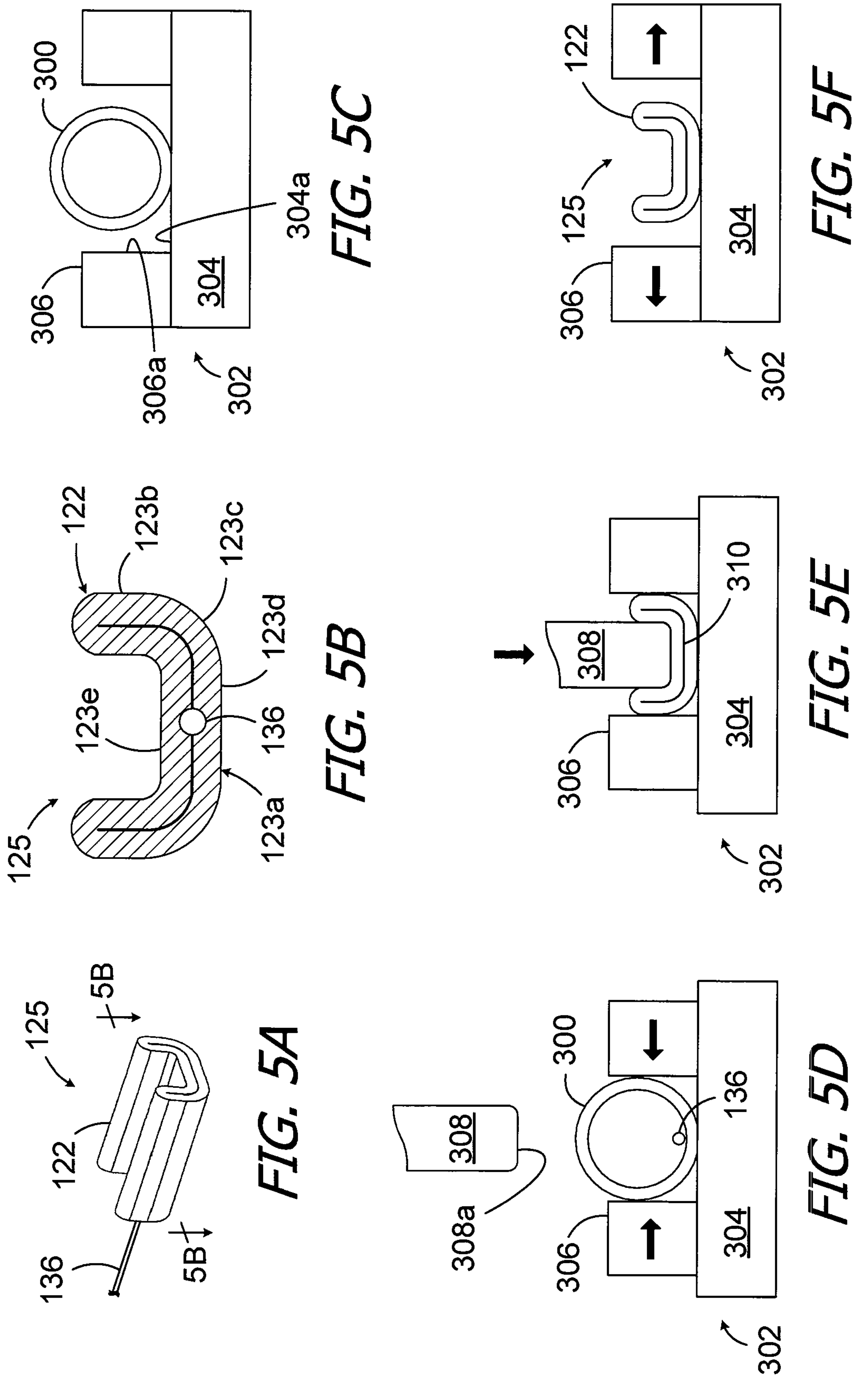
FIG. 5A is a perspective view of a portion of the cochlear lead electrode array illustrated in FIG. 4.
FIG. 5B is a section view taken along line 5B-5B in FIG. 5A.
FIG. 5C is an end view of a portion of a method in accordance with one embodiment of a present invention.
FIG. 5D is an end view of a portion of a method in accordance with one embodiment of a present invention.
FIG. 5E is an end view of a portion of a method in accordance with one embodiment of a present invention.
FIG. 5F is an end view of a portion of a method in accordance with one embodiment of a present invention.
Figure 5G:
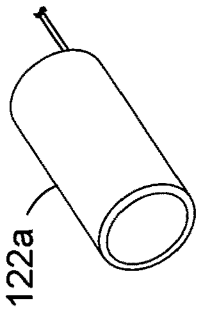
FIG. 5G is a perspective view of a portion of a cochlear lead electrode array in accordance with one embodiment of a present invention.

As illustrated for example in FIG. 4, the exemplary contacts 122 may be referred to in numbered order, 1st through 16th in the sixteen contact illustrated implementation, with the contact closest to the tip end 124 being the 1st contact and the contact closest to the base end 126 being the 16th contact. The contacts 122 are also the same size and shape in the illustrated implementation. Suitable materials for the contacts 122 include, but are not limited to, platinum, platinum-iridium, gold and palladium. Referring to FIGS. 5A and 5B, the exemplary contacts 122 may include a flat portion 123*a* and side portions 123*b* at the lateral ends of the flat portion 123*a*. The side portions 123*b* may be perpendicular to the flat portion 123*a* (as shown) or may have a different orientation relative to the flat portion. In the illustrated implementation, there are also curved portions 123*c* between the flat portion 123*a* and side portions 123*b*, and the contacts 122 define a flat U-shape. The flat portion 123*a* includes flat surfaces 123*d* and 123*e* that, in the illustrated embodiment, are parallel to one another.

A contact 122 and a lead wire 136 may together define a contact subassembly 125, and the contact subassembly may be formed by a placing a tubular workpiece into an appropriately shaped fixture (or "die"), placing the end of a lead wire into the workpiece, and then applying heat and pressure to the workpiece to compress the workpiece onto the lead wire. The insulation may be removed from the portion of the lead wire within the workpiece prior to the application of heat and pressure or during the application of heat and pressure. One exemplary method of forming the contact subassembly 125 is illustrated in FIGS. 5C-5F. Referring first to FIG. 5C, the exemplary method includes placing a contact workpiece 300 onto a die 302 (which is not a mold or part of a mold) that includes a base 304, with a flat surface 304*a*, and movable side members 306, with flat surfaces 306*a*. The exemplary contact workpiece 300 is a tube formed from the contact material. Although not limited to any particular shape, the exemplary workpiece 300 is a cylindrical tube and is circular in cross-section. The end of the associated lead wire 136 may be placed into the workpiece 300 (either before or after the workpiece is placed onto the die 302), and the movable side members 306 may be moved into contact with the workpiece 300, as is shown in FIG. 5D.

Next, as illustrated in FIGS. 5D and 5E, heat and pressure may be applied to the contact workpiece 300 with, for example, a weld tip such as the molybdenum weld tip 308, with a flat end surface 308*a*, in a resistance welding process. The compression and distortion of the workpiece 300 also cause portions of the workpiece to come into contact with one another along a seam 310 with the lead wire 136 therebetween. The flat surfaces 304*a* and 308*a* of the die base 304 and weld tip 308 create the flat surfaces 123*d* and 123*e* of the contact 122. The weld tip 308 may then be retracted, and the side members 306 may be moved outwardly, as shown in FIG. 5F. The completed contact subassembly 125 may then be removed from the die 302.

There are a variety of advantages associated with forming a contact subassembly, such as subassembly 125, in the manner described above. For example, forming the contact subassembly in a die (as compared to compressing a workpiece within the electrode array mold) prevents damage to the mold, allows contacts that are smaller than the associated portion of the mold and/or differently shaped than the associated portion of the mold to be employed, and allows damaged or otherwise non-conforming contacts to be identified and discarded prior to their inclusion in an electrode array. Other advantages associated with the present subassemblies are discussed below in the context of the exemplary molding method illustrated in FIGS. 16-20.

In other implementations, the contacts in an electrode array may be different in size and/or shape. For example, the contacts may be larger in the basal region than in the apical region. The contacts may be rings **122*a* (FIG. 5**G) that extend completely around the longitudinal axis LA in the apical region, or contacts that only extend about half-way around the longitudinal axis LA in the basal region. Alternatively, or in addition, the length (in the direction of the longitudinal axis LA) of the contacts in an electrode array may be the same or different.

As noted above, one or more of the windows 130 may be perimetrically offset from other windows of the electrode array 116, which facilitates accurate orientation of the windows 130 relative to the modiolus when the electrode array 116 (or portions thereof) is in a twisted state after the insertion into the cochlea. To facilitate this discussion, the contacts and windows are referred to generically herein as "contacts 122" and "windows 130," while references to specific contacts and windows include the contact number and window number, e.g., "contact 122-16" and "window 130-16." Referring to FIG. 6, as used herein, the perimeter of the electrode array 116 (which is the perimeter of the flexible body 120) is defined by the outer surface of the flexible body 120 in a plane perpendicular to the longitudinal axis LA, and the perimetric direction follows the perimeter around the electrode array 116 (and flexible body 120) in that plane, as is shown by arrow PD. The perimetric center PC of each window 130 is the mid-point of the window in the perimetric direction.

The exemplary electrode array 116 is configured for a situation in which the surgeon expects that the basal portion of the electrode array will not be twisted when the insertion is complete, while apical portion of the electrode array will twist in a relatively consistent manner from one contact 122 to the next. Accordingly, as can be seen in FIG. 4, the basal eight (8) windows 130, i.e., windows 130-16 to 130-9, are aligned with one another in the perimetric direction, while the apical eight (8) windows, i.e., windows 130-8 to 130-1, are offset from the basal windows in the perimetric direction in respective increments that increase from one window to the next. Although the present inventions are not limited to any particular perimetric offset or offset pattern, the windows 130-8 to 130-1 are offset by the same amount from one parametric center PC to next. As a result, the respective portions of the contacts 122-8 to 122-1 that are exposed by way of the windows 130-8 to 130-1 are not the same. The respective portions of the contacts 122-8 to 122-1 that are exposed by way of the windows 130-8 to 130-1 are also different than the portions of contacts 122-16 to 122-9 that are exposed by way of the windows 130-16 to 130-9. By way of example, but not limitation, in other implementations, the perimetric offsets may begin in the more basal windows (e.g., window 130-13) or may begin in the more apical windows (e.g., window 130-4). The magnitude of the perimetric offsets may also vary. As is discussed in greater detail below with reference to FIG. 26, the parametric positions may be selected based on patient-specific information or averages associated with known insertion data.

Figure 6:
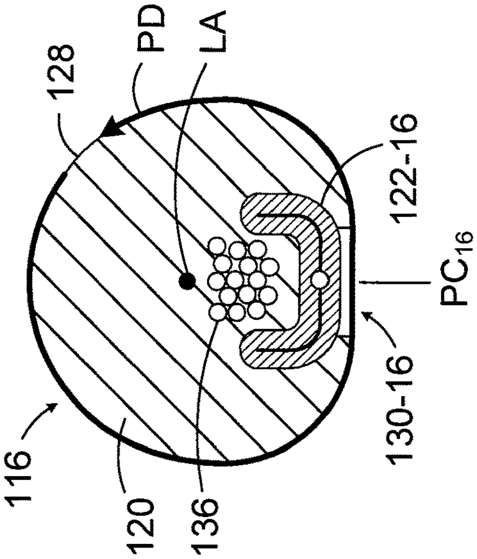
FIG. 6 is a section view taken along line 6-6 in FIG. 4.
Figure 7:
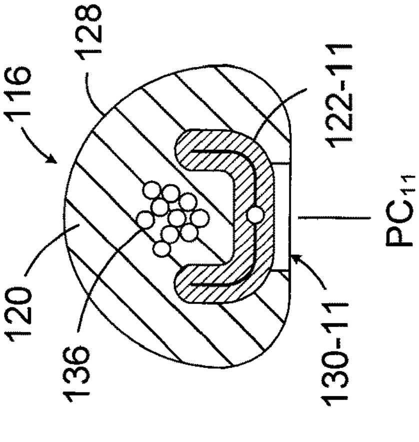
FIG. 7 is a section view taken along line 7-7 in FIG. 4.
Figure 8:
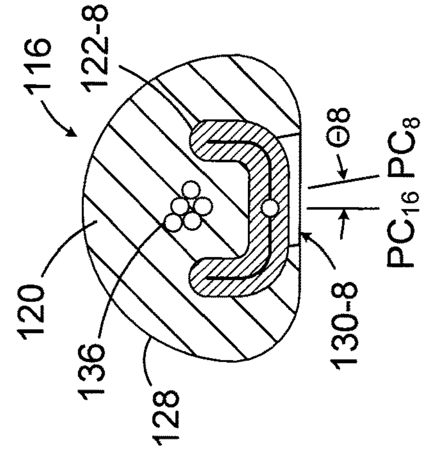
FIG. 8 is a section view taken along line 8-8 in FIG. 4.
Figure 9:
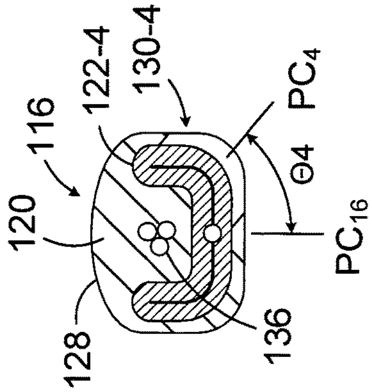
FIG. 9 is a section view taken along line 9-9 in FIG. 4.
Figure 10:
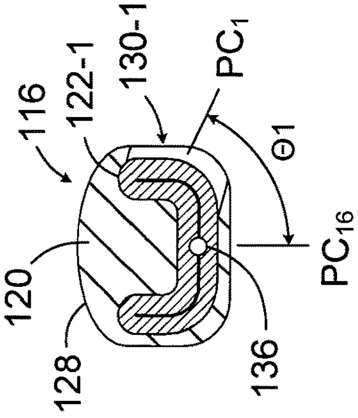
FIG. 10 is a section view taken along line 10-10 in FIG. 4.

The window and parametric center locations of the exemplary electrode array 116 in a non-twisted state are illustrated in FIGS. 6-10. Referring first to FIGS. 6 and 7, which are cross-sections taken through contacts 122-16 and 122-11, the associated windows 130-16 and 130-11 have perimetric centers $PC_{16}$ and $PC_{11}$ that are aligned with one another in the parametric direction PD. The perimetric center $PC_8$ of the window 130-8 associated with contact 122-8 (FIG. 8), on the other hand, is offset in the perimetric direction PD from the perimetric center $PC_{16}$ of the window 130-16 (as well as from the perimetric centers of windows 130-15 to 130-9) by angle θ8. Although the present inventions are not so limited, angle θ8 is about 10° in the illustrated implementation, and the angle of each successive perimetric offset is about 10° from the adjacent offset. As used herein in the context of angles, the word "about" means ±3-5°. The perimetric center $PC_4$ of the window 130-4 associated with contact 122-4 (FIG. 9) is offset in the perimetric direction from the perimetric center $PC_{16}$ of the window 130-16 (as well as from the perimetric centers of windows 130-15 to 130-9) by angle θ4, which is equal to about 50° in the illustrated implementation. The perimetric center $PC_1$ of the window 130-1 associated with apical-most contact 122-1 (FIG. 10) is offset in the perimetric direction from the perimetric center $PC_{16}$ of the window 130-16 (as well as from the perimetric centers of windows 130-15 to 130-9) by angle θ1, which is equal to about 80° in the illustrated implementation.

The contact windows 130 in the exemplary implementation are the same size and shape. However, in other implementations, the contact windows in an electrode array may be different in size in the longitudinal direction and/or in the perimetric direction and/or different in shape. For example, the windows may be larger in the basal region than in the apical region. Alternatively, or in addition, the spacing between the windows may also be varied. For example, in those instances where the length of the windows in the longitudinal direction is less than that of the contacts, the distance between the windows may be varied even when the distance between the contacts is the same.

Figure 11:
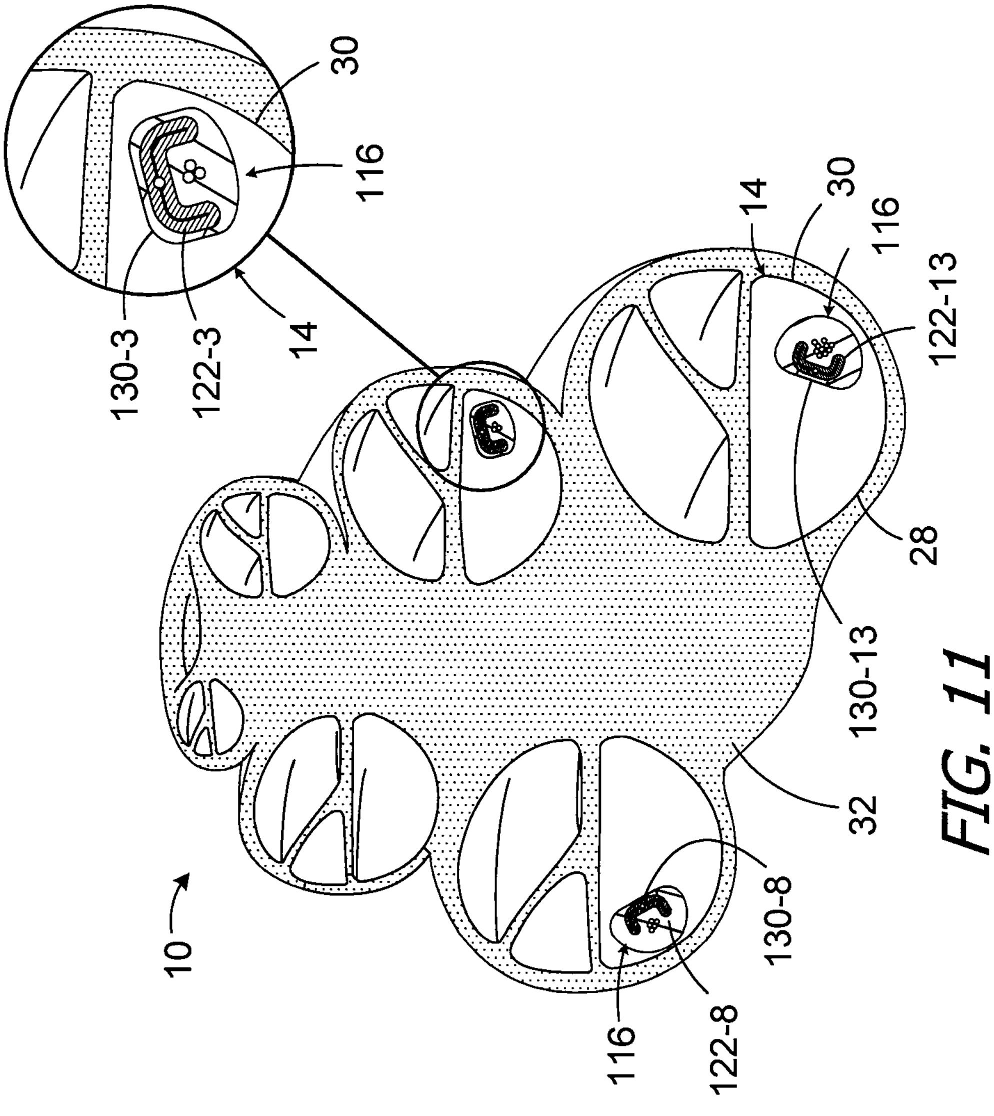
FIG. 11 is a section view of the cochlear electrode array illustrated in FIGS. 3-10 positioned within a cochlea.

Turning to FIG. 11, it can be seen that despite the twisting of the exemplary array 116 within the scala tympani 14, the windows 130 are facing the medial wall 28 and the modiolus 32. In particular, the portion of the electrode array 116 that include contacts 122-1 to 122-8 (and windows 130-1 to 130-8) has twisted, and contacts 122-3, 122-8 and 122-13 (and windows 130-3, 130-8 to 130-13) are visible is the illustrated section view. Despite the twisting of the apical portion of the electrode array 116, the windows 130-3 and 130-8 (and the exposed portions of contacts 122-3 and 122-8) are facing the medial wall 28 and the modiolus 32, as is the window 130-13 (and the exposed portion of contact 122-13) in the untwisted basal portion.

Figure 11A:
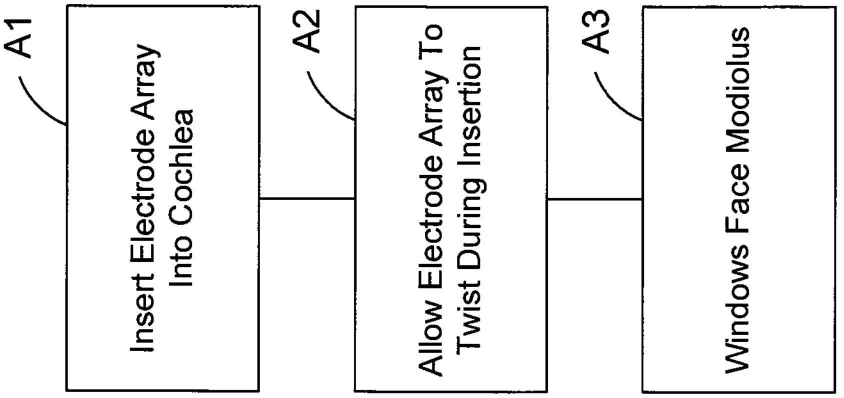
FIG. 11A is a flow chart showing a method in accordance with one embodiment of a present invention.

Put another way, and referring to FIG. 11A, the exemplary electrode array 116 may be inserted into the cochlea. [Step A1.] At least a portion of the electrode array is allowed to twist a predetermined (or "known" or "anticipated") amount around the longitudinal axis LA of the flexible body 120 of the electrode array 116. [Step A2.] The perimetric offset of the windows 130 in the portion of the electrode array 116 that is allowed to twist is such that, when the electrode array is fully inserted into the cochlea and has twisted the predetermined amount, the windows on both the twisted and non-twisted portions of the electrode array will face the modiolus. [Step A3.]

Figure 11B:
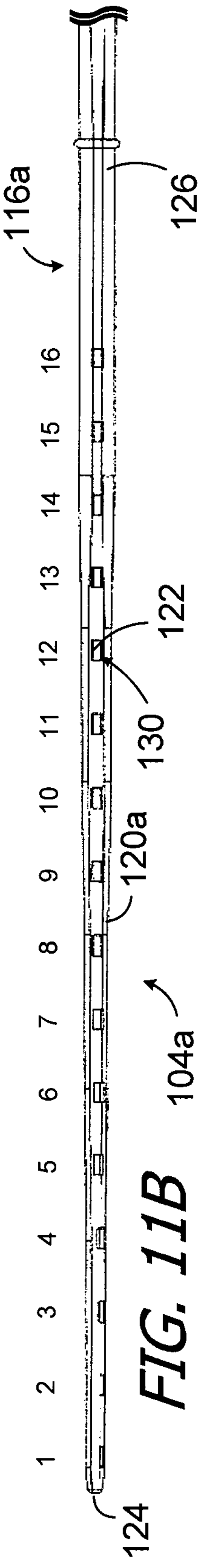
FIG. 11B is a bottom view of a cochlear lead electrode array in accordance with one embodiment of a present invention.
Figure 12:
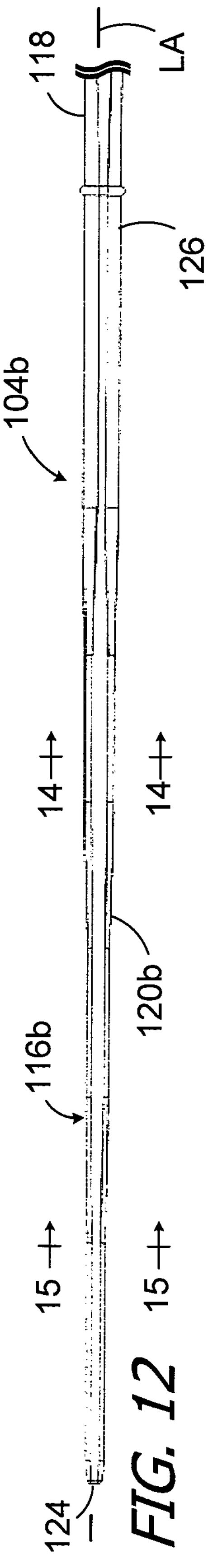
FIG. 12 is a bottom view of a cochlear lead blank in accordance with one embodiment of a present invention.
Figure 13:
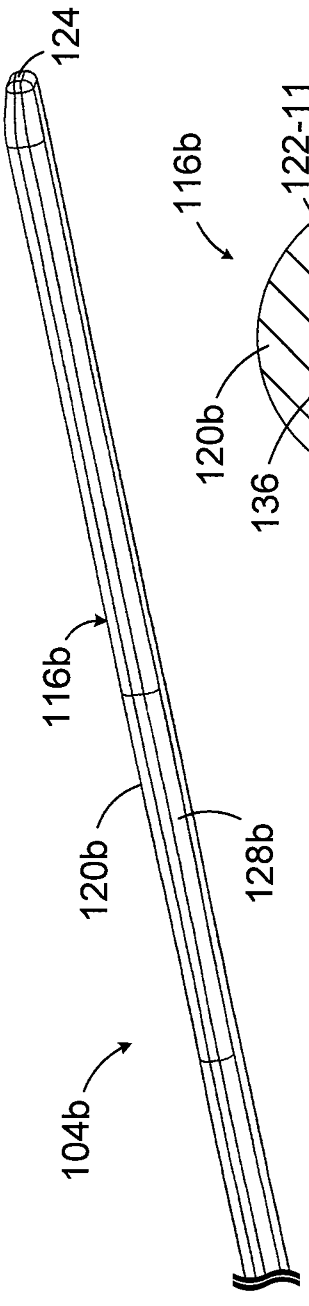
FIG. 13 is a perspective view of the cochlear lead blank illustrated in FIG. 12.
Figure 14:
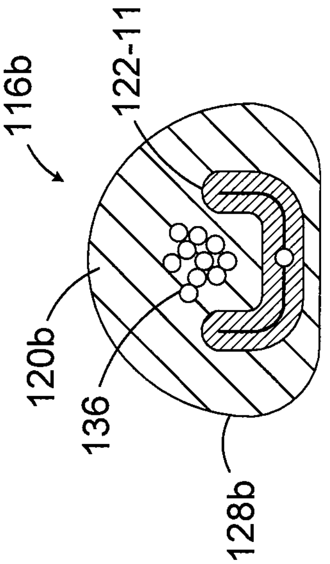
FIG. 14 is a section view taken along line 14-14 in FIG. 12.
Figure 15:
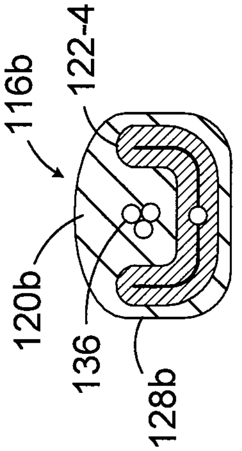
FIG. 15 is a section view taken along line 15-15 in FIG. 12.

In other embodiments, the electrode array flexible body may be stiffer in the basal region in order to limit or prevent twisting of the basal region of the electrode array. Referring to FIG. 11B, the exemplary cochlear lead 104*a* illustrated therein is essentially identical to cochlear lead 104 and similar element are identified by similar reference numerals. To that end, the cochlear lead 104*a* includes an electrode array 116*a* with a flexible body 120*a*, a plurality of conductive contacts 122 and a corresponding plurality of windows 130. Here, however, a basal portion of the electrode array 116*a* (e.g., from the basal end 126 to contact 122-8) is stiffer that the remainder of the electrode array and, accordingly, resists twisting more that the same portion of the electrode array 116. The increased stiffness may be accomplished in any suitable manner. For example, in the illustrated implementation, the stiffer basal portion of the flexible body 120*a* is formed from stiffer material than the remainder of the flexible body. Alternatively, or in addition, contact sizes/shapes that result in electrode arrays (or portions thereof) that are less likely to twist may be employed.

In accordance with another invention herein, cochlear leads having various differing window orientations and/or configurations may be formed from a common cochlear lead blank from which material is removed to form the windows. One example of such a cochlear lead blank is generally represented by reference numeral 104*b* in FIGS. 12-15. The exemplary cochlear lead blank 104*b* is identical to the cochlear lead 104, but for the absence of windows, and similar elements are represented by similar reference numerals. To that end, the exemplary cochlear lead blank 104*b* includes an electrode array blank 116*b* as well as the wing 118. In other implantations, the wing 118 may be omitted and added to a completed electrode array (if so desired). The exemplary electrode array blank 116*b* has a flexible body 120*b* and a plurality of electrically conductive contacts 122 (e.g., the sixteen contacts 122 illustrated in FIG. 4) spaced along the flexible body between the tip end 124 and the base end 126. The contacts 122 are located inward of the flexibly body outer surface 128*b*. There are no windows 130 and, given the lack of windows, the contacts 122 are completely covered by the electrically non-conductive material that forms the flexible body 120*b* and are not exposed. The windows 130 may be formed in a cochlear lead blank such as blank 104*b* in, for example, the manner described below with reference to FIGS. 21-25.

Figure 16:
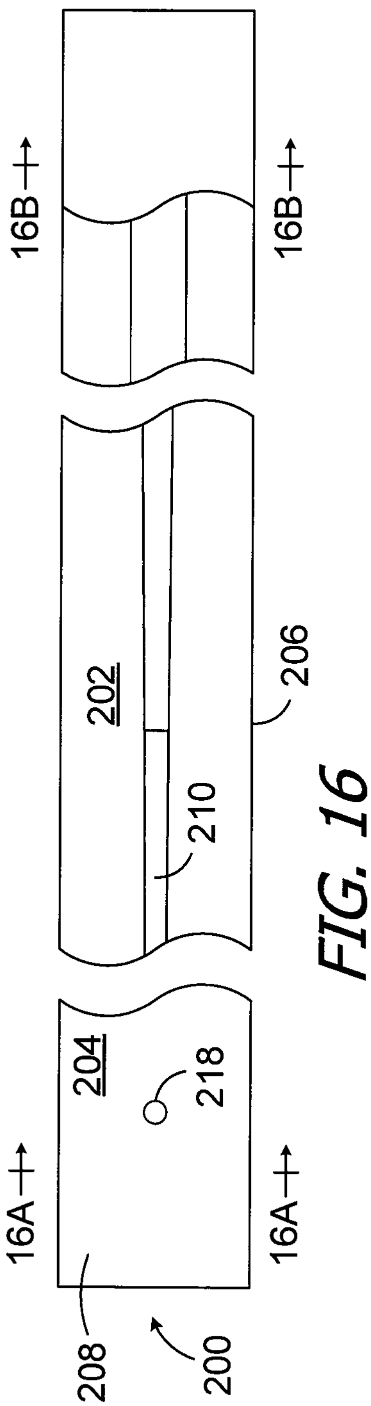
FIG. 16 is a top view of a mold in accordance with one embodiment of a present invention.
Figure 16B:
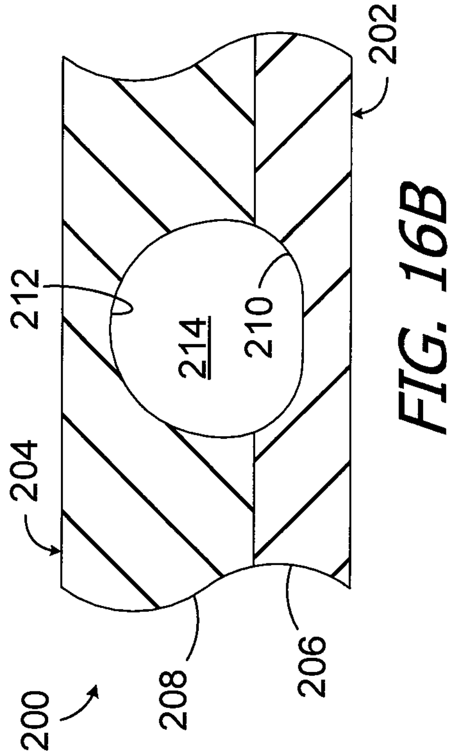
FIG. 16B is a section view taken along line 16B-16B in FIG. 16.
Figure 16A:
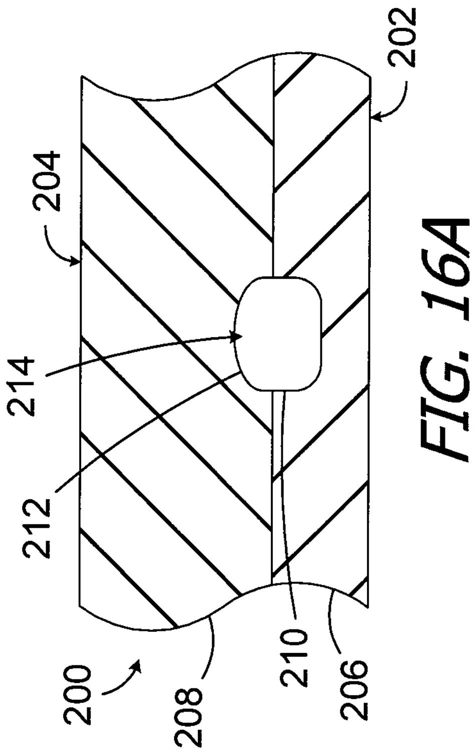
FIG. 16A is a section view taken along line 16A-16A in FIG. 16.

One exemplary method of forming a cochlear lead blank, such as the cochlear lead blank 104*b* illustrated in FIGS. 12-15, or merely the electrode array 116*b*, may involve the use of the exemplary mold 200 illustrated in FIGS. 16-16B. Mold 200 has first and second mold parts 202 and 204. The first and second mold parts 202 and 204 include respective plates 206 and 208 with surfaces 210 and 212 that together define an elongate cavity 214 in the shape of the cochlear lead blank 104*b*. The second mold part 204 also includes one or more inlets 218 for the injected LSR (or other resilient material) that forms the flexible body 120. Indicia 220*a* and/or 220*b* (FIG. 16C) may be provided, on the top surface of mold plate 206 and/or on the cavity defining surface 210, at the locations of each of the contacts 112-1 to 112-16.

Figure 16C:
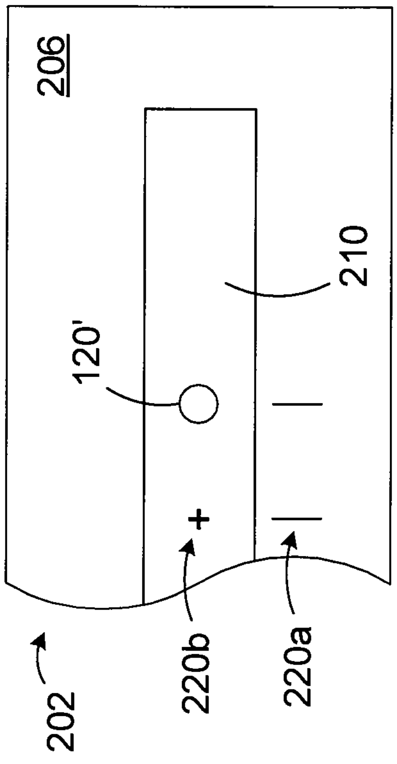
FIG. 16C is a top view of a portion of a method in accordance with one embodiment of a present invention.
Figure 16D:
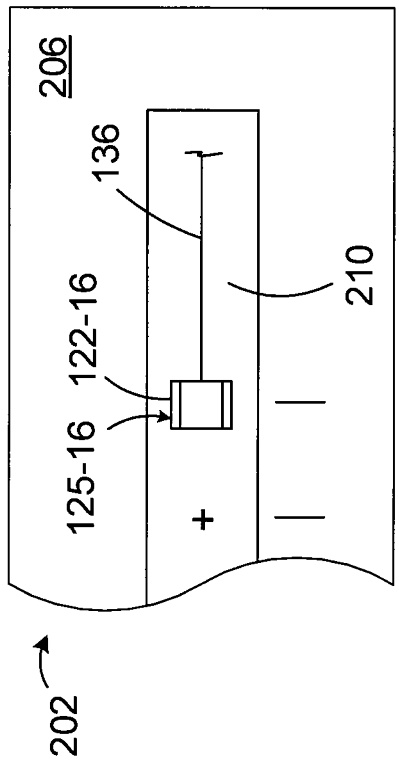
FIG. 16D is a top view of a portion of a method in accordance with one embodiment of a present invention.

While the second mold part 204 is detached from the first mold part 202, the contact subassemblies 125, i.e., the contacts 122 with the lead wires 136 attached, may be placed on the cavity defining surface 210 of the mold part 202 in, for example, the manner illustrated in FIGS. 16C-16F. For example, the contact subassemblies 125 may be placed onto the first mold part 202 in series, beginning with the subassembly that includes contact 122-16 and ending with the subassembly that includes contact 112-1. The placement of the contact assemblies 125 onto the mold surface may be accomplished by hand or through the use of a robot. To that end, the indicia 220*a* and 220*b* may be optimized for the human eye and/or for robotic guidance instrumentalities. Referring first to FIG. 16C, a small quantity of resilient material 120' may be deposited onto the mold surface 210 at the location of contact 122-16. A contact subassembly 125-16, including contact 122-16 and a lead wire 136, may be placed onto the resilient material 120' in the manner illustrated in FIG. 16D. The resilient material 120', once cured, will secure the contact 122-16 to the mold surface 210, thereby preventing movement of the contact assembly 125-16 from the intended location and intended orientation relative to the mold surface.

Figure 16E:
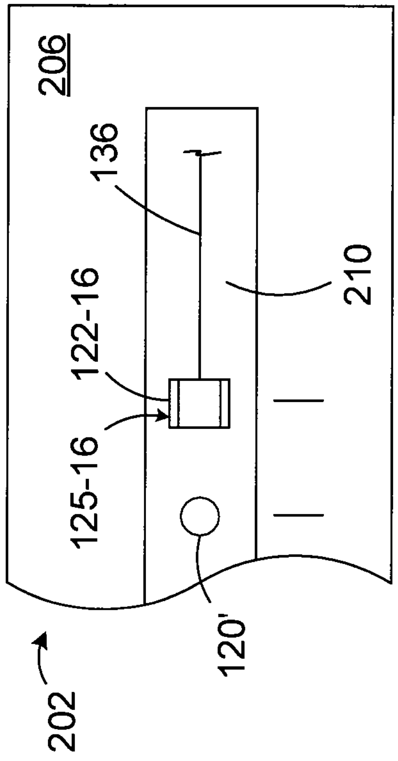
FIG. 16E is a top view of a portion of a method in accordance with one embodiment of a present invention.
Figure 16F:
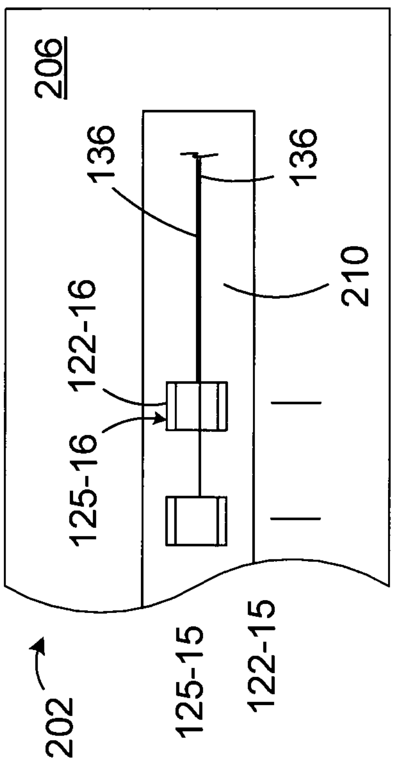
FIG. 16F is a top view of a portion of a method in accordance with one embodiment of a present invention.

Turning to FIG. 16E, a small quantity of resilient material 120' may be deposited onto the mold surface 210 at the location of the next contact, i.e., contact 122-15. The contact subassembly 125-15, including contact 122-15 and a lead wire 136, may be placed onto the resilient material 120' in the manner illustrated in FIG. 16F. The lead wire 136 associated with subassembly 125-15 will extend over the previously positioned contact 122-16 to and beyond the base end of the mold (the right end in the orientation illustrated in FIGS. 16 and 16C-16F). This process may then be repeated for the contact assemblies associated with contacts 122-14 to 122-1.

The resilient material 120' will become part of the blank flexible body 120*b* during the molding process. Suitable resilient material 120' includes, but is not limited to, any of the resilient materials described above that are used to form the flexible body 120. It should also be noted that, in some implementations and depending upon curing time, all of the quantities of resilient material 120' may be deposited onto the mold surface 210 prior to the placement of any of the contact subassemblies 125. In other implementations, a subset of the quantities of resilient material 120' may be deposited onto the mold surface 210 followed by a corresponding subset of contact subassemblies 125 being placed onto the resilient material.

Figure 17:
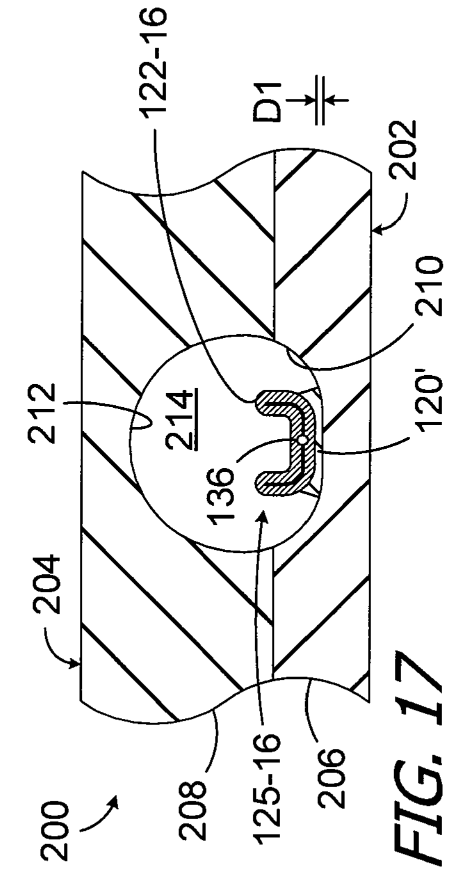
FIG. 17 is a section view of a portion of a method in accordance with one embodiment of a present invention.
Figure 18:
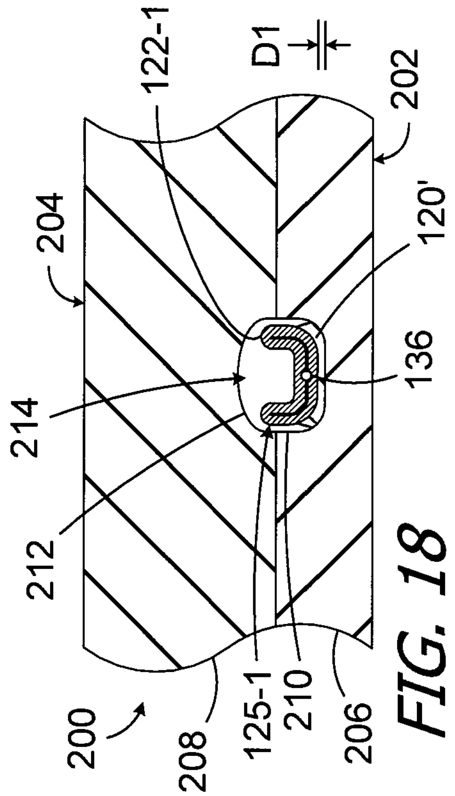
FIG. 18 is a section view of a portion of a method in accordance with one embodiment of a present invention.
Figure 19:
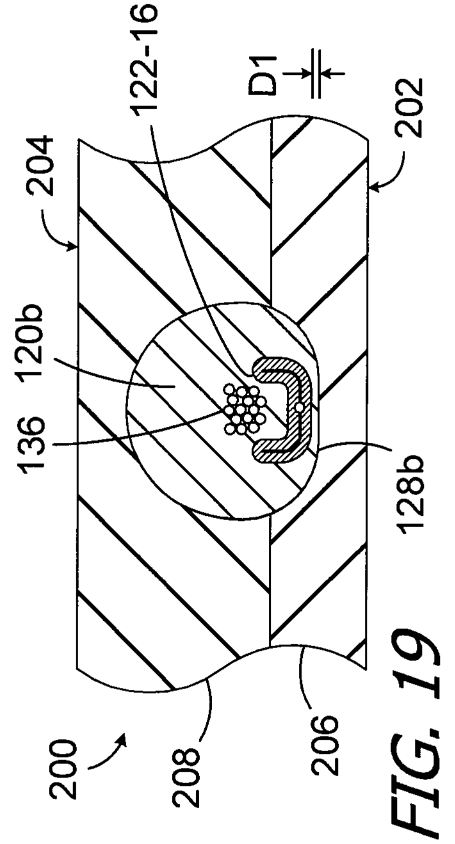
FIG. 19 is a section view of a portion of a method in accordance with one embodiment of a present invention.
Figure 20:
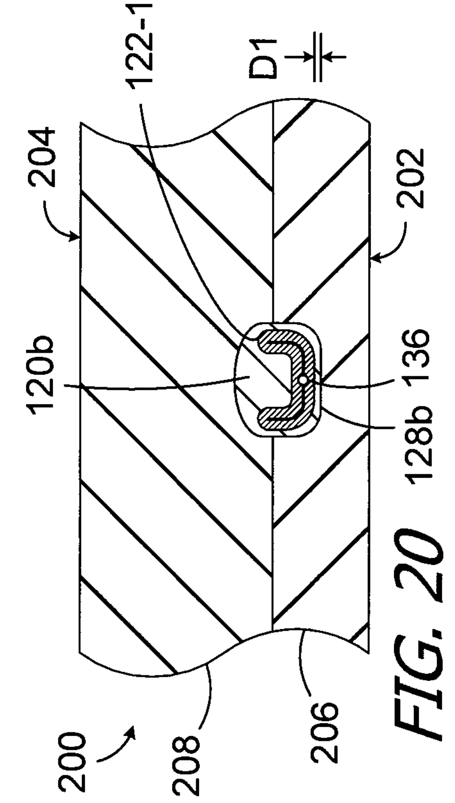
FIG. 20 is a section view of a portion of a method in accordance with one embodiment of a present invention.

Once all of the contact subassemblies 125 have been positioned in the first mold part 202, the second mold part 204 may be placed over the first mold part 202 to complete the mold 200 in the manner illustrated in FIGS. 17 and 18. A clamp, screws or other suitable instrumentality (not shown) may be used to hold the mold parts 202 and 204 together. The LSR or other suitable resilient material may then be injected (or otherwise introduced) into the mold cavity 214 to form the flexible body 120. The resilient material 120' separates the contacts from the surface 210 by a distance D1 (FIGS. 17 and 18) in addition to holding the contacts in place 122. As a result, the surfaces of the contacts 122 that are adjacent to the bottom surface of the mold cavity 214 are located inwardly from the exterior surface 128*b* and the associated portions of the flexible body 120*b* by the distance D1, and are covered by the flexible body. The remainders of the contacts 122 are also covered by the flexible body 120*b* due to the differences in size of contacts 122 and the cavity 214 as well as the manner in which the contacts are positioned within the cavity. After the resilient material hardens, the mold parts 202 and 204 may be separated from one another. The completed cochlear lead blank 104*b* may be removed from the cavity 214.

One exemplary process for forming the windows 130 in the cochlear lead blank 104*b* to create a cochlear lead 104 is illustrated in FIGS. 21-25. The cochlear lead blank 104*b* may be placed onto a fixture 250 that is configured to hold the blank in a linear and untwisted state. To that end, the exemplary fixture 250 includes a plate 252, with a groove 254, and a plurality of suction apertures 256. The suction apertures 256 are connected to a source of negative pressure (not shown) by a suction line 258. The suction force holds the cochlear lead blank 104*b* firmly in place. Portions of the flexibly body 120*b* corresponding to the windows 130-1 to 130-16 are then removed from the cochlear lead blank 104*b*, thereby exposing the portions of contacts 122-1 to 122-16, to complete the electrode array 116. In some instances, the cochlear lead blank 104*b* may be reoriented on a particular fixture, or moved to a different fixture, during the window formation process.

Figures 21, 22, 23, 24, 25:
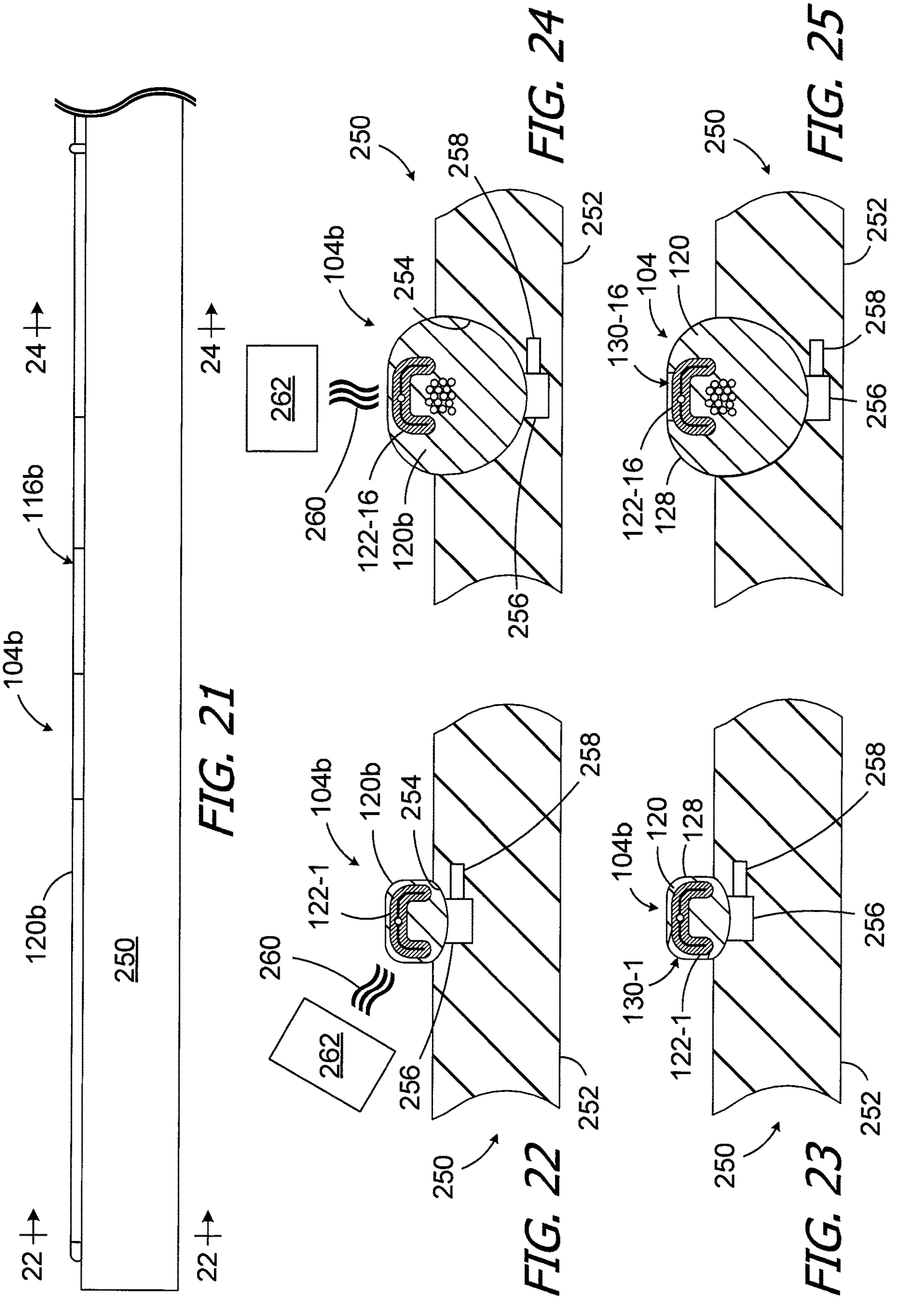
FIG. 21 is a side view of a portion of a method in accordance with one embodiment of a present invention.
FIG. 22 is a section view of a portion of a method in accordance with one embodiment of a present invention.
FIG. 23 is a section view of a portion of a method in accordance with one embodiment of a present invention.
FIG. 24 is a section view of a portion of a method in accordance with one embodiment of a present invention.
FIG. 25 is a section view of a portion of a method in accordance with one embodiment of a present invention.

Any suitable instrumentality or process may be used to remove material from the cochlear lead blank 104*b* to form the windows 130 and expose portions of the contacts 122. By way of example, but not limitation, ablation energy 260 (e.g., a laser beam) from an ablation energy source 262 is used to remove material from the cochlear lead blank 104*b* to form the windows 130 and expose portions of the contacts 122 in the illustrated embodiment. Referring for example to FIGS. 22 and 23, ablation energy 260 may be applied to the cochlear lead blank 104*b* to form the window 130-1 that is associated with the contact 122-1. Turning to FIGS. 24 and 25, ablation energy 260 may be applied to the cochlear lead blank 104*b*, and at a location that is parametrically and longitudinally offset from the location illustrated in FIGS. 22 and 23, to form the window 130-16 that is associated with the contact 122-16. The remainder of the windows 130 may be formed in the same way. Other exemplary methods of removing material from a cochlear lead blank include, but are not limited to chemical etching, masking, acid washing, electro-dissolution, electrical discharge machining and mechanical removal (e.g., surface abrasion such as rubbing or grit blasting).

Figure 26:
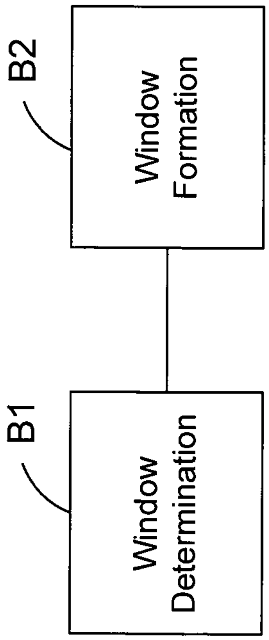
FIG. 26 is a flow chart showing a method in accordance with one embodiment of a present invention.

One exemplary process for producing a cochlear lead from a cochlear lead blank is summarized by the flow chart illustrated in FIG. 26. First, in step B1, the particular features of the contact windows (e.g., parametric orientations and offsets, sizes, spacings, etc.) for the particular cochlear lead are determined. In some instances, the determination is a patient-specific determination that is based on patent-specific data, such as patient scans and/or tonotopic mapping, that can be used to predict rotation of the electrode array within the cochlea (e.g., with physical three-dimensional modeling of the particular patient's scanned cochlea and/or computer simulations of the electrode array insertion into the particular patient's scanned cochlea). The patient-specific scan and/or tonotopic mapping data may also be fed into predictive software, so that the ideal window orientations, offsets, etc. to counteract the predicted effects of rotation can be identified. In those instances where the determinations are not patient-specific, averages based on known cochlea shapes and insertion data may be used. For example, window orientations for a typical left cochlea insertion and window orientations for a typical right cochlea insertion may be determined. Next, in step B2, the windows 130 are formed in a cochlear lead blank, in the manner described above, based on the determined parametric offsets and other window features.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A method of forming an electrode array, comprising the steps of:

securing a plurality of contact subassemblies to a mold surface at longitudinally spaced locations within a mold solely by depositing uncured resilient material directly onto the mold surface and thereafter placing the contact subassemblies on top of the uncured resilient material that was deposited directly onto the mold surface such that the uncured resilient material that was deposited directly onto the mold surface prior to placement of the contact subassemblies is located between and in contact with both the contact subassemblies and the mold surface, the contact subassemblies including, prior to being placed into the mold, an electrically conductive contact having a flat portion defining lateral ends and side portions associated with the lateral ends of the flat portion and a lead wire secured to the electrically conductive contact;

after the uncured resilient material, which was deposited directly onto the mold surface prior to placement of the contact subassemblies and is located between and in contact with both the contact subassemblies and the mold surface, has cured and secured the plurality of contact subassemblies to the mold surface, introducing additional resilient material into the mold to form an electrode array blank including a flexible body defining an exterior surface and the electrically conductive contacts below the exterior; and forming a plurality of windows in the electrode array blank that extend through the exterior surface of the flexible body to the electrically conductive contacts.

2. The method claimed in claim 1, wherein the electrically conductive contacts comprise tubular workpieces that have been compressed; and a portion of each lead wire is located between parts of the compressed tubular workpiece to which the lead wire is secured.

3. The method claimed in claim 1, wherein the lead wires are secured to the flat portions of the electrically conductive contacts.

4. The method claimed in claim 1, wherein the electrically conductive contacts define a flat U-shape.

5. The method claimed in claim 1, wherein the side portions of the electrically conductive contacts are perpendicular to the flat portion.

6. The method claimed in claim 1, wherein the electrically conductive contacts include curved portions between the flat portion and the side portions.

7. The method claimed in claim 1, wherein all of the electrically conductive contacts define the same shape.

8. The method claimed in claim 1, wherein the flat portion of the electrically conductive contacts defines first and second flat exterior surfaces that are parallel to one another and face in opposite directions.

9. The method claimed in claim 8, wherein the windows extend to the first flat exterior surfaces of the electrically conductive contact flat portions.

10. The method claimed in claim 1, wherein introducing resilient material into the mold comprises injecting resilient material into the mold.

11. The method claimed in claim 1, wherein the resilient material that secures the contact subassemblies to the mold surface is the same as the resilient material that is introduced into the mold to form the electrode array blank.

12. The method claimed in claim 1, wherein the resilient material that secures the contact subassemblies to the mold surface is different than the resilient material that is introduced into the mold to form the electrode array blank.

13. The method claimed in claim 1, wherein the step of forming a plurality of windows comprises removing material from the flexible body.

14. The method claimed in claim 13, wherein removing material from the flexible body comprises laser ablating material from the flexible body.

* * * * *